United States Patent [19]
Armstrong

[11] 3,986,862
[45] Oct. 19, 1976

[54] EMULSIFIABLE LIQUID CONCENTRATES CONTAINING 4-AMINO-6-T-BUTYL-3-(METHYLTHIO)-1,2,4-TRIAZIN-5-ONE AND 2-CHLORO-N-(2,6-DIETHYLPHENYL)-N-METHOXYMETHYLACETAMIDE

[75] Inventor: Johnny Leroy Armstrong, Hockessin, Del.

[73] Assignee: E. I. Du Pont de Nemours and Company, Wilmington, Del.

[22] Filed: July 3, 1974

[21] Appl. No.: 485,740

[52] U.S. Cl. .................................. 71/93; 71/118; 71/DIG. 1
[51] Int. Cl.$^2$ ........................................ A01N 9/22
[58] Field of Search .................... 71/93, 118, DIG. 1

[56] References Cited
UNITED STATES PATENTS

| | | | |
|---|---|---|---|
| 3,442,945 | 5/1969 | Olin | 71/93 |
| 3,671,523 | 6/1972 | Westphal et al. | 71/93 |

*Primary Examiner*—Lewis Gotts
*Assistant Examiner*—Catherine L. Mills

[57] ABSTRACT

Chemically and physically stable herbicidal, water-emulsifiable, liquid concentrates containing 4-amino-6-t-butyl-3-(methylthio)-1,2,4-triazin-5-one (metribuzin) and 2-chloro-N-(2,6-diethylphenyl)-N-methoxymethylacetamide (alachlor) are dissolved with an appropriate emulsifying agent in chlorobenzene. The concentrates contain an unexpectedly large amount of metribuzin and alachlor at relatively low temperatures, indicating the existence of solvent synergism.

4 Claims, No Drawings

EMULSIFIABLE LIQUID CONCENTRATES CONTAINING 4-AMINO-6-T-BUTYL-3-(METHYLTHIO)-1,2,4-TRIAZIN-5-ONE AND 2-CHLORO-N-(2,6-DIETHYLPHENYL)-N-METHOXYMETHYLACETAMIDE

BACKGROUND OF THE INVENTION

The use of

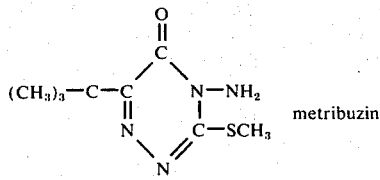

Formula I and

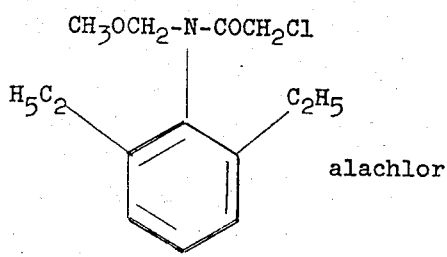

Formula II known, respectively, as metribuzin and alachlor, as herbicides is well known in the art. Alachlor is ordinarily dissolved with an emulsifying agent in chlorobenzene.

In the past, metribuzin and alachlor had been shipped individually and then used to control broad-leaf and grassy weeds in certain beneficial plants.

There are often occasions when one may wish to apply these materials together in order to get the benefit of both kinds of herbicidal activity. In those instances, it is desirable to form a combination product which provides economies of packaging and shipping, makes it convenient to prepare a slurry spray and avoids dosage errors.

SUMMARY OF THE INVENTION

According to this invention, it has unexpectedly been found that metribuzin and alachlor may be dissolved with an appropriate emulsifying agent in chlorobenzene with the unexpected result that at certain ratios the total amount of metribuzin and alachlor which can be dissolved is higher than the total amount which could be dissolved separately in chlorobenzene.

The weight ratio of metribuzin to alachlor may vary from approximately 1:9 to 1:1. In general, the chlorobenzene solvent will contain from 3–6 pounds of total active ingredient per U.S. gallon of solution. The solution will also contain a surfactant or surfactants possessing a suitable hydrophylic/lipophilic balance to serve as emulsifying agent for the concentrate in water. The particular surfactant or surfactants utilized are not critical, and appropriate surfactants would be obvious to one skilled in the art.

Metribuzin and alachlor may be characterized by the following formulae: 4-amino-6-t-butyl-3-(methylthio)-1,2,4-triazin-5-one (metribuzin) and 2-chloro-N-(2,6-diethylphenyl-N-methoxymethylacetamide (alachlor).

DETAILED DESCRIPTION

In more detail, the instant invention relates to the unexpected finding that when one combines metribuzin and alachlor in designated weight ratios, solvent synergism is observed in chlorobenzene. That is to say, when one adds, in the designated ratio, 3–6 pounds of total active ingredient of metribuzin and alachlor per U.S. gallon of solution in chlorobenzene, one is able to dissolve an unexpectedly large amount of active ingredient in the solvent. The designated weight ratio of metribuzin to alachlor is from 1:9 to 1:1, preferably from 1:5 to 2:3, and most preferably from 1:4 to 1:2.

Metribuzin and alachlor can be prepared by methods known in the art. Preparation of metribuzin is disclosed generally in Belgian Pat. No. 697,083, the disclosure of which is herein incorporated by reference. The preparation of alachlor is disclosed in U.S. Pat. No. 3,442,945, the disclosure of which is herein incorporated by reference.

The formulation disclosure of the Belgian patent discloses the use of chlorobenzene as a solvent and mixtures of the compounds of the Belgian patent with other herbicides, such as ureas, triazines, etc.; there is no teaching to the use of a mixture of metribuzin and alachlor.

Similarly, the U.S. patent teaches mixtures of alachlor and other herbicides; here again, however, there is no teaching to the mixture of the instant invention.

The selection of a suitable surfactant or mixture of surfactants to serve as emulsifying agent can be made readily by one skilled in the art. The procedure for selecting such a surfactant is to be found in *Emulsions, Theory and Practice* by Paul Becher, 2nd Ed., Reinhold Publishing Corporation, N.Y. The disclosure of this book is herein incorporated by reference. Suitable surfactants can also be selected from those listed in *Detergents and Emulsifiers*, published by McCutcheon's Division, Allured Publishing Corporation, N.J., 1972 Annual, which is herein incorporated by reference.

The preferred emulsifiers are nonionic and anionic surfactants with a hydrophylic/lipophilic balance (HLB) suitable to emulsify the concentrates of this invention in water.

Particular surfactants or emulsifiers which may be utilized include the following: ATLOX 3403F or ATLOX 3408 which are general purpose formulated nonionic, anionic emulsifiers available from ICI, Unites States; and WAYFOS M100, anionic complex organic (aromatic) phosphate ester in free acid form, which is available from Wayland Chemical Div. of Philip A. Hunt Chemical Corporation.

The amount of emulsifier which will be utilized may vary between about 0.5 to 20 wt.%, preferably about 2 to 5 wt.%.

The unexpected solvent synergism between alachlor, metribuzin and chlorobenzene is illustrated in the Table below. This Table shows the temperature to which the solution can be cooled before crystals of active ingredient precipitate and settle out. When metribuzin is the only material in chlorobenzene only 4% can be held in solution at −6° C. This is equivalent to about 0.35 lbs. metrubuzin/gallon. Solutions more concentrated than that could not be stored at the commercially important warehousing conditions at or near the conventional freezing temperatures (32° F. or 0° C.). If on the other hand metribuzin and alachlor within the designated ratios are present, the low temperature storage characteristics are greatly improved. As the Table shows, for example 8.6% metribuzin and 34.6% alachlor in chlorobenzene solvent have a crystallization temperature (sometimes referred to as freezing temperature) below −6° C. These concentrations represent 0.8 lbs. of metribuzin and 3.2 lbs. of alachlor per gallon. The metribuzin content thus is more than twice the content possible in the absence of alachlor, and the total mixed active concentration is 4 lb./gal. The Table which follows demonstrates other favorable low temperature characteristics of the synergistic system of the invention.

TABLE

SOLUBILITY OF METRIBUZIN AT LOW TEMPERATURES IN LASSO* AND/OR CHLOROBENZENE

| % Metribuzin | % Alachlor | Ratio (App.) | Solvent | Incipient Crystallization Temperature (° C.) |
|---|---|---|---|---|
| 4 | 0 | — | Chlorobenzene | −6 |
| 8.0 | 40.2 | 1:5 | Lasso + Chlorobenzene | <0 |
| 8.6 | 34.6 | 1:4 | Lasso | <<−6 |
| 9.8 | 39.4 | 1:4 | Lasso | <0 |
| 10.2 | 39.2 | 1:4 | Lasso | <−6 |
| 12.7 | 38.1 | 1:3 | Lasso | <0 |
| 12.5 | 25.0 | 1:2 | Lasso | ≈0 |

*Lasso is a product of the Monsanto Company, a 43.7% alachlor formulation in chlorobenzene with a suitable surfactant.

EXAMPLE 1

Twenty grams of metribuzin are dissolved in 175.5 grams of Lasso and an additional 24.5 grams of chlorobenzene. This solution may be filtered to clarify the solution if necessary. This solution consists of 34.6% alachlor (4 parts) and 8.6% metribuzin (1 part) and has a density of 1.12 g/cc at room temperature (~22° C). This translates to 0.81 lb. alachlor per qt. (3.24 lb/gal) and 0.20 lb. metribuzin per qt. (0.8 lb/gal). After three weeks accelerated storage in the freezer to depress chemical decomposition and in an oven at 45° C. to accelerate chemical decomposition, assay test results indicate good chemical stability.

EXAMPLE 2

Fourteen and one-half grams of metribuzin and 18.2 grams of alachlor are dissolved in 62.3 grams of chlorobenzene and 5.0 grams of "Atlox 3403F", a blend of nonionic and anionic emulsifiers from ICI, United States, having an HLB of 13.0. The solution is then filtered. This solution contains a 4:5 mixture of metribuzin to alachlor, which is a three-pound total of active ingredient per gallon. The freeze point of this solution is 0° C.

EXAMPLE 3

Metribuzin (10.7 grams) and alachlor (42.8 grams) are dissolved in 41.5 grams of chlorobenzene. Five grams of "Atlox 3403F" emulsifier is added and dissolved. The solution is filtered to remove insoluble particulate matter by any of a number of techniques understood by those skilled in the art. This concentrate contains one pound of metribuzin and four pounds of alachlor which is a five-pound total of active ingredient per gallon. The freeze point of this solution is about 0° C.

EXAMPLE 4

Metribuzin (6.55 grams) and alachlor (58.95 grams) and 5.0 grams of "Atlox 3403F" are dissolved in 29.5 grams of chlorobenzene and filtered. This solution contains a total of 6 pounds total active ingredient per gallon in a ratio of 1 part metribuzin to 9 parts of alachlor. The freeze point of this solution is approximately 0° C.

I claim:
1. A herbicidal concentrate which has improved solubility comprising from 3 to 6 pounds per U.S. gallon of a mixture of (A) 4-amino-6-t-butyl-3-(methylthio)-1,2,4-triazin-5-one and (B) 2-chloro-N-(2,6-diethylphenyl)-N-methoxymethylacetamide in chlorobenzene, the ratio of A to B being 1:9 to 1:1, in the presence of surfactant to emulsify the concentrate in water.
2. A composition of claim 1 wherein the ratio of A to B is 1:5 to 2:3.
3. A composition of claim 2 wherein the ratio of A to B is 1:4 to 1:2.
4. The composition of claim 1 wherein the surfactant is present in the amount of about 0.5 to 20 wt.%.

* * * * *